(12) United States Patent
Ercan (10) Patent No.: US 9,878,111 B2
(45) Date of Patent: Jan. 30, 2018

(54) UPPER EXTREMITY SUPPORT DEVICE FOR VASCULAR IMAGING

(71) Applicant: Ertugrul Ercan, Izmir (TR)

(72) Inventor: Ertugrul Ercan, Izmir (TR)

(73) Assignee: ERTUGRUL ERCAN, Izmir (TR)

( * ) Notice: Subject to any disclaimer, the term of this patent is extended or adjusted under 35 U.S.C. 154(b) by 241 days.

(21) Appl. No.: 14/429,946

(22) PCT Filed: Sep. 20, 2012

(86) PCT No.: PCT/TR2012/000149
§ 371 (c)(1),
(2) Date: Mar. 20, 2015

(87) PCT Pub. No.: WO2013/154509
PCT Pub. Date: Oct. 17, 2013

(65) Prior Publication Data
US 2015/0246186 A1    Sep. 3, 2015

(51) Int. Cl.
| | |
|---|---|
| *A61B 5/05* | (2006.01) |
| *A61M 5/52* | (2006.01) |
| *A61B 6/04* | (2006.01) |
| *A61B 6/00* | (2006.01) |
| *A61G 13/12* | (2006.01) |
| *A61M 5/00* | (2006.01) |
| *A61G 13/00* | (2006.01) |

(52) U.S. Cl.
CPC .............. *A61M 5/52* (2013.01); *A61B 6/0421* (2013.01); *A61B 6/0485* (2013.01); *A61B 6/504* (2013.01); *A61B 6/548* (2013.01); *A61G 13/0045* (2016.11); *A61G 13/124* (2013.01); *A61G 13/1235* (2013.01); *A61G 13/1265* (2013.01); *A61M 5/007* (2013.01); *A61M 2205/3331* (2013.01)

(58) Field of Classification Search
CPC .................... A61M 5/52; A61M 5/007; A61M 2205/3331; A61G 13/0045; A61G 13/1265; A61G 13/124; A61G 13/1235; A61B 6/548; A61B 6/0485; A61B 6/504; A61B 6/0421
USPC .................................. 600/407–500
See application file for complete search history.

(56) References Cited

U.S. PATENT DOCUMENTS

| 4,858,903 A | 8/1989 | Tari et al. |
| 2004/0193061 A1* | 9/2004 | Sato ........................ A61B 5/02 600/500 |

FOREIGN PATENT DOCUMENTS

| DE | 202010012488 U1 | 11/2010 |
| EP | 1980226 A1 | 10/2008 |

* cited by examiner

*Primary Examiner* — Sanjay Cattungal
(74) *Attorney, Agent, or Firm* — Avery N. Goldstein; Blue Filament Law PLLC (57) ABSTRACT

The present invention is an operation device that can be used for angiographic operations applied on the upper extremity, comprising a hand-finger fixing apparatus (1), wrist air bag (8) located between preferably the arm support part (13) and hand-finger fixing apparatus (1), a length adjustment apparatus (22) on the arm support part (13), an elbow air bag (9), a housing support part (11), one level adjustment apparatus (23) located on the housing support part (11), a flexible connection band (6), a power and a pneumatic pumping system (2) and a and a remote control unit.

18 Claims, 6 Drawing Sheets

UPPER EXTREMITY SUPPORT DEVICE FOR VASCULAR IMAGING

The present invention which is an assist device developed for applying an angiographic process on the arm relates to an angiography assist device suitable for the anatomy of the arms, having a pneumatic air sac on the wrist and elbow part, providing a lengthwise shortening movement, moving up and down.

The present invention can be used in the angiographic processes applied with iodic liquid not penetrating X-ray and called as opaque substance. During the angiographic processes, a needle should go into the vascular system of the patient. Inguinal artery can be selected for this process, however the comfort is not provided for the patient during this process. Upon the process applied on the inguinal artery, local bleedings called as hematoma occur more frequently. In order to overcome such problems, brachial arteries are selected ever-increasingly. The difficulty in this selection is the need to work on an artery of relatively small size. Therefore the doctors applying the process refrain from making angiography on the brachial artery.

In order to apply angiography on the brachial artery, the patient should lie on his/her back on the angiography device table. In the meanwhile his/her arm should be extending to the side in a straight position without being twisted on the elbow part.

In the state of the art, simple arm supports are used to support the arm of the patient during the angiography. These supports are rectangular hard objects of the same length with the harm of the patient. While the patient is lying on his/her back, his/her arm stays stable on this object in a position extending to the side. Until recently, these supports haven't been designed as ergonomically to the arm of the patient. While the said objects were being designed, the outwards physiological angle of the front arm has not been taken into consideration. Likewise, it could not provide an outward extension (dorsiflexion) movement to the hand necessary for applying the process. When it is considered that the arm length and structures of the people may vary depending on their sex, age, form, etc., the need for adjusting the length of the support to be placed under the arms during the process comes out. However the length of the arm support used within the state of the art cannot be shortened in its own axis.

The arm support apparatuses used in the state of the art are in a direction parallel with the arm and cannot move up and down, from top to toe. Moreover, in the case that the arm support of the patient stay up or down, in order to move the patient support device towards the bottom of the patient arm, the patient should stand up and lie again, and then he/she should take the necessary position again.

Figure 1:
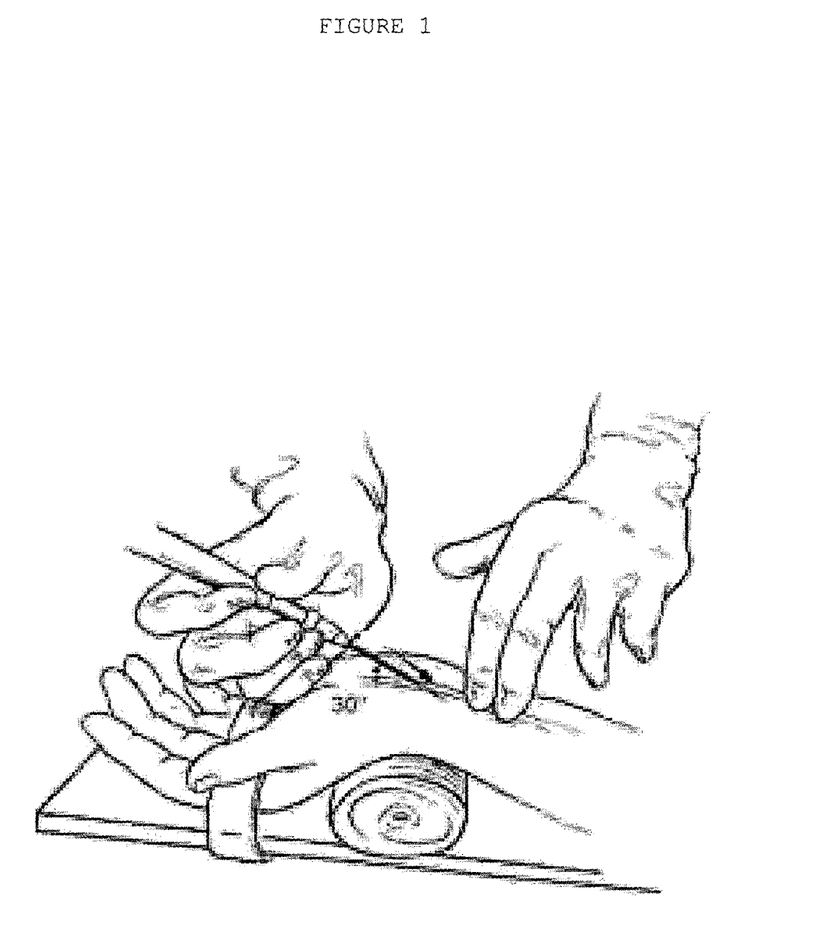
FIG. 1. The view of the support apparatus used within the state of the art
Figure 2:
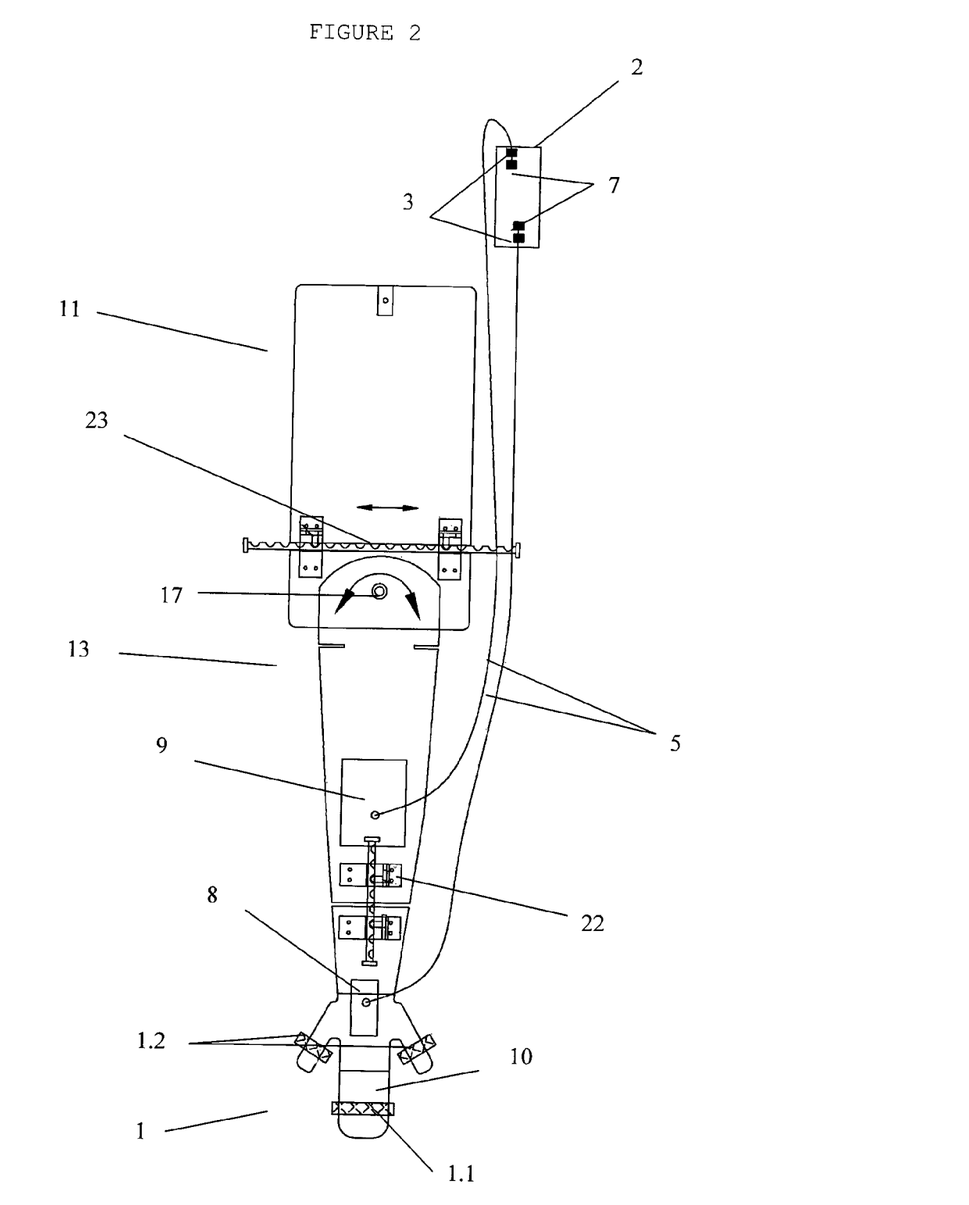
FIG. 2. The top view of the operation device

For the angiography processes applied on the arm, the radial, brachial, axillary arteries are selected as the artery. For an angiography process on the radial artery, the wrist part of the patient should be stretch, and the hand should be stretched backwards when the palm is open facing the top. In this position, the artery comes closer to the skin, and therefore it assumes a position more appropriate for the puncture into the artery. Therefore within the state of the art, wrist rolls are used for this purpose. The roll is located between the support device and the wrist and thus the wrist can assume a stretched position (FIG. 1).

In the case that the brachial artery present in the elbow is used, the elbow should be partially upheld. Therefore roll-like objects to keep the elbow in an upwards stable position are used.

The most important reason lying behind the unsuccessful angiographic operations that have been planned on the arm arteries is that the arm cannot be made to assume the desired position. In such a case, it becomes very difficult to puncture the artery with a needle. The need of being sterilized for the doctor during the operation prevents him/her from touching the patient directly, however in the systems according to the state of the art, the doctors may be obliged to intervene manually in order to get the arm of the patient in an appropriate position. This causes a microbial pollution because of doctor's direct touch on the patient.

Another important problem experienced within the systems according to the present invention is that the upholding apparatuses like a roll or etc. that are located under the wrist or elbow are stable. The change in the position of the patient, the displacement of the system with an arm movement, being in stable sizes and being discomfortingly hard are the problems experienced within the state of the art. When different positions or uprisings are needed while the operation is being carried out, as the patient is covered with a sterilized cloth, the operation is continued by the operation technician under the table.

DESCRIPTION OF THE FIGURES

FIG. 3. The side view of the operation device

DESCRIPTION OF THE PARTS

1. Hand-finger fixing apparatus
1.1. Middle block projection
1.2. Edge projection
2. Power and pneumatic pumping system
3. Selenoid valve
4. Bedding platform
5. Air hose
6. Flexible connection band
7. Pressure sensor
8. Wrist air bag
9. Elbow air bag
10. Hand placing platform
11. Housing support part
12. Connection means for housing support part
13. Arm support part
14. Level adjustment shaft part
15. Level adjustment fixing pin
16. Level adjustment bedding housing part
17. Arm support part movement pin
18. Arm extending shaft part
19. Fixing pin for arm extending part
20. Arm extending housing part
21. Hand fixing bands
22. Length adjustment apparatus
23. Level control apparatus The operation device that can be used for the angiographic operations applied on the arms according to the present invention is designed as appropriate to the arm anatomy of the patients. The air sacs filled with air to provide an easy operation on the arteries of the patient with needle can be controlled with a remote control and the arm of the patient is made to take the appropriate position. The elbow parts of the patients are enabled to extend outwards physiologically. In order for the hand wrist to get an angle in a way that the palm will face upwards, the wrist part gets an angle backwards.

In the tall or short patients, in order for the differences in the arm length not to affect the anatomic placement, the arm of the support device can be shortened or extended by the operator. Moreover, the angiography arm support device can be moved up and down in a parallel manner with the table axis. And also, the angiography arm support device can be rotated to the left or right in accordance with the patient position.

Instead of the under-wrist or under-elbow upholding rolls or prothesis that may be needed to get an appropriate localization under the skin of the radial or brachial arteries, air bags improving the comfort of the patient are used. Thanks to these objects, the wrist or elbow of the patient can be upheld in a desired extent.

Within the present invention, as the angle and position of the arm of the patient can be changed by the user doctor when desired by means of the operation device, all of the problems experienced in the stable apparatuses used in the state of the art are eliminated. Therefore, the operation flaws emerging during the angiographic operations are prevented and the success ratio of the angiographic operations is increased.

Likewise, thanks to the control of the present invention, the hygiene problems (infection risk) emerging when the doctor touches on the patient during the application of the angiographic operation are prevented. Within the present invention, the doctor does not need to touch on the patient for controlling the system or adjusting the arm position any more. The user can control the system and therefore the position of the patient's arm by means of a remote control.

Thanks to the operation device according to the present invention, the wrist and the elbow can be upheld and made to assume a position by means of air sacs. This upholding and positioning process can be stopped whenever desired. The desired measurements are determined with a millimetric sensitivity. Therefore the success ratio of the operation can be increased, the artery puncture is made easier, the artery can be cannulated with a needle more easily, the operation reaches to success with fewer attempts, and the patient fells less pain.

As the system described within the present invention has anatomically more appropriate structure and configuration, the arm of the patient can stay on the system more easily. As the structure can change its lengthwise axis and as its size parallel to the angiography table can change, it is possible for the system to be adjusted to different arm lengths without requiring the patient to move. Therefore the comfort of the patient is improved.

An operation device according to the present invention which can be used for angiographic operations applied on the arm comprises a hand-finger fixing apparatus (1) which has been designed to be larger than the edge projections (1.2) of a preferably middle block projection (1.1) at the edge of the arm support part (13) or to form a bifurcated structure; at least one wrist air bag (8) located between preferably the arm support part (13) and hand-finger fixing apparatus (1); preferably a length adjustment apparatus (22) on the arm support part (13), which can change the length of the operation device in accordance with the arm length of the patient; an elbow air bag (9) located preferably on the rear part of preferably the length adjustment apparatus (22) on the arm support part (13); a housing support part (11) designed in a rectangular form connected to the rear part of preferably the arm support part (13) by means of a movement pin (17) of the arm support part; at least one level adjustment apparatus (23) located on the housing support part (11); a flexible connection band (6) connected to preferably the rear part of the housing support part (11) with a connection means (12) for housing support part; a power and a pneumatic pumping system (2) connected to the elbow air bag (9) and wrist air bag (8) by means of air pipes (5); and a remote control unit that can be used for operating the system.

Figure 4:
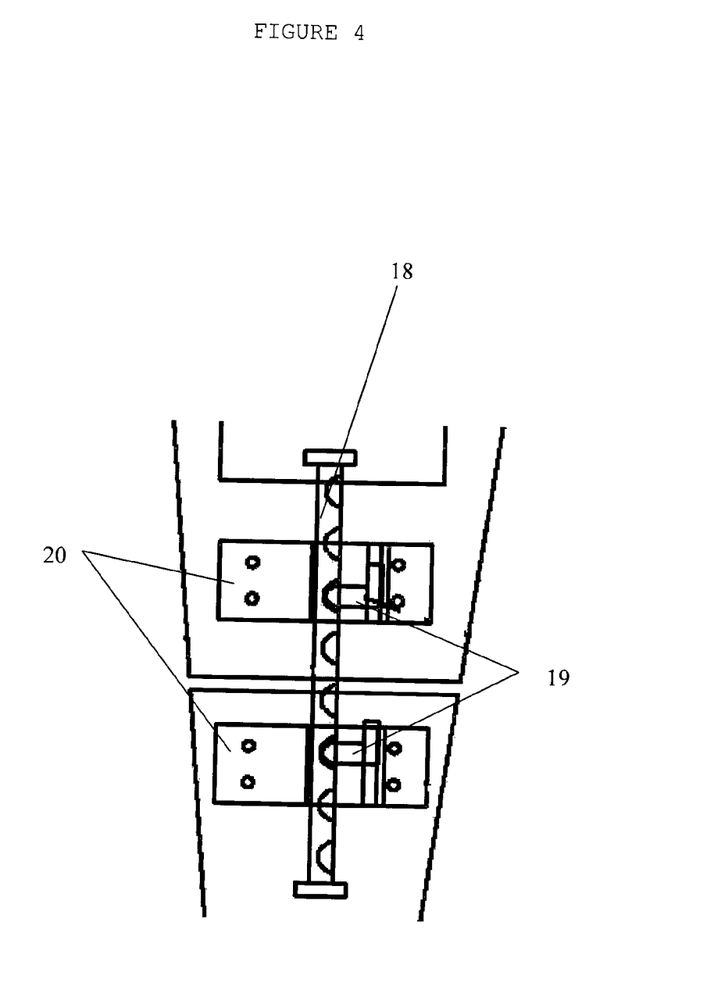
FIG. 4. The detailed view of the length adjustment apparatus

The length adjustment apparatus (22) described above comprises preferably at least two arm extending housing parts (20) fixing the structure to the arm support part (13); arm extending part fixing pins (18) preferably located one for each arm extending housing part (20), which is designed in the form of a stick or projection fitted on the arm extending housing part (20); at least one arm extending shaft part (18) which can be fixed to the arm extending part fixing pins (18) or moved on the arm extending housing part (20), which extends in a parallel manner to the arm support part (13) plane and comprises indents appropriate for the dented or stick structure on the arm extending part fixing pin (19).

In the case that the user desires to extend the length of the arm support part (13), he/she moves the arm extending shaft part (18) to a direction parallel with the extending direction of the arm support part (13), and the arm extending shaft part (18) leaves the arm extending part fixing pin (19) which is holding it and therefore can extend the length of the arm support part (13) by moving. Likewise, when the user desires to shorten the length of the arm support part (13), he/she can manage to do so by changing the position of the arm extending shaft part (18).

Figure 5:
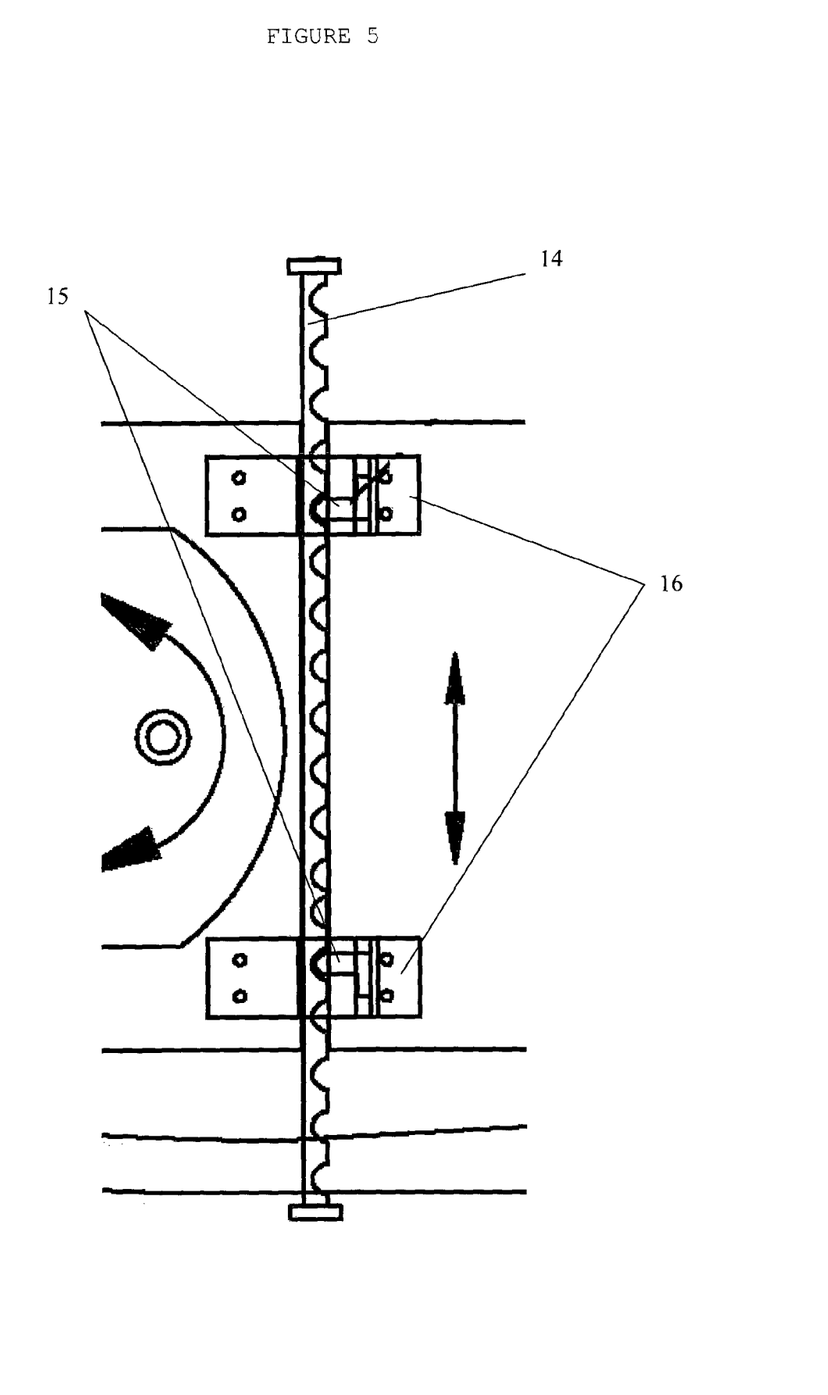
FIG. 5. The detailed view of the level controlling device
Figure 6:
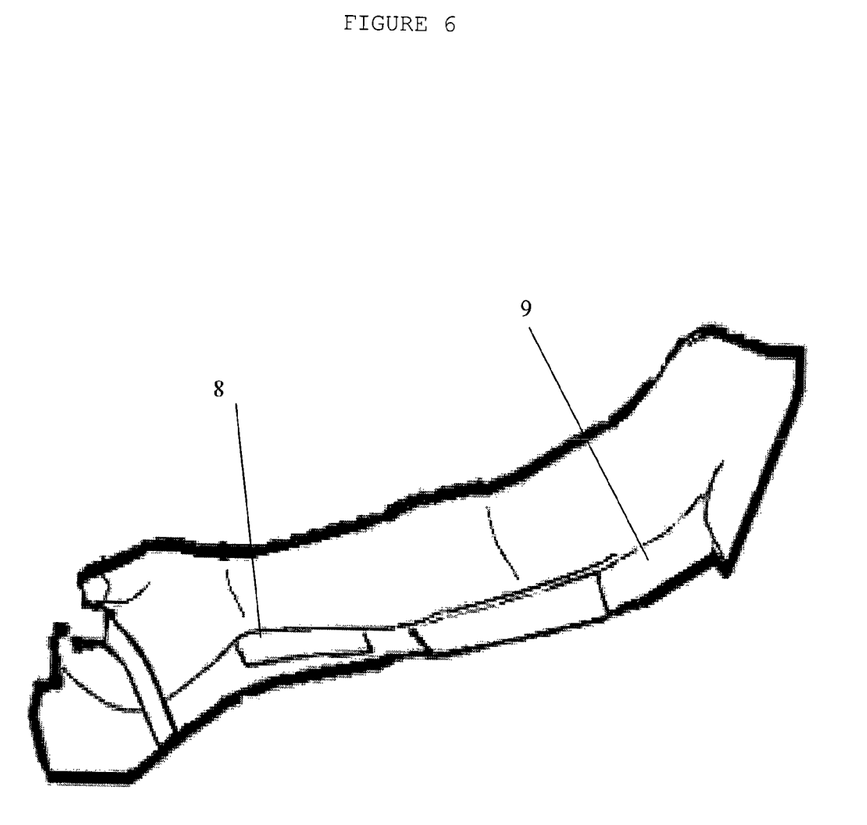
FIG. 6. The view of the operation device when it is connected to the arm

The level adjusting apparatus (23) described above comprises preferably at least two level adjustment housing parts (16) fixing the structure to the housing support part (11); level adjusting fixing pin (15) preferably located one for each level adjusting housing part (16) designed in the form of a stick or a dent fixed on the level adjusting housing part (16); at least one level adjustment shaft part (14) comprising indents appropriate for the stick and dent structure on the level adjustment fixing pin (15) extending vertically to the plane of the housing support part (11), which can be fixed to the arm extending part fixing pins (18) or moved on the arm extending housing part (20).

Like in the length adjustment apparatus (22), the user can change the position of the level adjustment shaft part (14) on the horizontal plane, comprised in the level adjustment apparatus (23), and therefore he/she can change the position of the arm support part (13) on the horizontal plane as well.

When desired, an engine can be connected to the length adjustment apparatus (22) and to the level adjustment apparatus (23), and the length adjustment apparatus (22) and the level adjustment apparatus (23) can be controlled with an electrical engine by means of a remote control.

An arm support part movement pin (17) is located between the housing support part (11) and the arm support part (13). Therefore the arm support part (13) can move independently from the housing support part (11) on the horizontal plane in a way that it takes the arm support part movement pin (17) as the center. As a result, when it is desired to change the inclination of the patient's arm on the horizontal plane, the arm support part (13) can be moved and adjusted.

The arm support part movement pin (17) is located on the bedding platform (4) extending as a flat body at the end part of the arm support part (13).

The power and pneumatic pumping system (2) described above comprises at least one selenoid valve (3) for each air pipe (5) regulating the air flow into the system, and at least one pressure sensor (7) for each air pipe (5) which can control the air inside the system and therefore control inflation of the wrist air bag (8) and the elbow air bag (9).

When the user desires to change the height of the patient's arm, he/she can change the pressure of the air inside the wrist air bag (8) and elbow air bag (9) either together or separately by using the remote control. Therefore the user can millimetrically adjust the position of the patient's arm for each coordinate axis.

A flexible connection band (6) connected to the housing support part (11) by means of a housing support part connection means (12) is connected on the rear part of the housing support part (11). Therefore the operation device can be mounted to the housing. This connection cuff can easily be removed. None of the structures that are used are radio-opaque. Therefore the interaction with the images obtained from the angiography device is prevented.

The hand-finger fixing apparatus (1) mentioned above is designed in a way that it will be bigger than preferably the edge projections (1.2) of the middle block projection (1.1) and it will form a bifurcated structure. The middle block projection (1.1) is inclined to hold the middle three fingers of the patient and to be proper for the palm structure of the patient, and therefore a hand-placing platform (10) is created within the structure. In order for the fingers of the patient to be fixed, the middle block projection (1.1) and the edge projections (1.2) comprise hand-fixing bands (21) on which the fingers can be fixed.

The air bags used within the present invention are UV stabilized, appropriate for medical use, not allowing gas air leakage, resistant to high air pressure, resistant to high air volumes, semi compliant, of 300 µm medical polyurethane, and rectangular. While creating the structure, thermal welding method is used.

The invention claimed is:

1. An operation device for angiographic operations applied on an arm of a patient, comprising:
    a hand-finger fixing apparatus (1) which has been designed to be larger than edge projections (1.2);
    at least one wrist air bag (8);
    a length adjustment apparatus (22) which can change a length of the operation device in accordance with the arm length of the patient;
    an elbow air bag (9);
    a housing support part (11) connected to an arm support part (13);
    at least one level adjustment apparatus (23) located on the housing support part (11);
    a flexible connection band (6);
    a power and pneumatic pumping system (2) connected to the elbow air bag (9) and wrist air bag (8) by air pipes (5); and
    a remote control unit used for operating the system;
    wherein a height of the arm is changed by changing the pressure of air inside the wrist air bag (8) and elbow air bag (9) either together or separately by using the remote control.

2. The operation device of claim 1, wherein the length adjustment apparatus (22) comprises at least two arm extending housing parts (20) fixing the hand-finger fixing apparatus to the arm support part (13); arm extending part fixing pins (19); and at least one arm extending shaft part (18) which can be fixed to the arm extending part fixing pins (19) or moved on the arm extending housing part (20), which extends in a parallel manner to the arm support part (13) plane and has indents appropriate for the dented or stick structure on the arm extending part fixing pin (19).

3. The operation device of claim 2, wherein a length of the arm support part (13) is extended by moving the arm extending shaft part (18) to a direction parallel with the extending direction of the arm support part (13), and the arm extending shaft part (18) leaves the arm extending part fixing pin (19) which is holding it and therefore can extend the length of the arm support part (13) by moving.

4. The operation device of claim 1, wherein the level adjustment apparatus (23) comprises at least two level adjustment housing parts (16) fixing the structure to the housing support part (11); leveling an adjusting fixing pin (15) located one for each level adjusting housing part (16) designed in the form of a stick or a dent fixed on the level adjusting housing part (16); and at least one level adjustment shaft part (14) having indents appropriate for the stick and dent structure on the level adjustment fixing pin (15) extending vertically to the plane of the housing support part (11), which can be fixed to the level adjusting pins (15) or moved on the level adjusting housing part (16).

5. The operation device of claim 4, wherein by changing a position of the said level adjustment shaft part (14) on a horizontal plane, the position of the arm support part (13) on the horizontal plane can be changed as well.

6. The operation device of claim 1, wherein the level adjustment apparatus (23) and length adjustment apparatus (22) are controlled with an electrical engine by said remote control.

7. The operation device of claim 1, wherein the flexible connection band (6) is connected to the housing support part (11) at a rear part of the housing support part.

8. The operation device of claim 2, wherein the arm extending part fixing pins (19) are located one for each arm extending housing part (20), which is designed in the form of a stick or projection fitted on the arm extending housing part (20).

9. An operation device for angiographic operations applied on an arm of a patient, comprising:
    a hand-finger fixing apparatus (1) which has been designed to be larger than edge projections (1.2);
    at least one wrist air bag (8);
    a length adjustment apparatus (22) which can change a length of the operation device in accordance with the arm length of the patient;
    an elbow air bag (9);
    a housing support part (11) connected to an arm support part (13);
    at least one level adjustment apparatus (23) located on the housing support part (11);
    a flexible connection band (6);
    a power and pneumatic pumping system (2) connected to the elbow air bag (9) and wrist air bag (8) by air pipes (5); and
    a remote control unit used for operating the system;
    wherein an arm support part movement pin (17) is located between the housing support part (11) and arm support part (13), enabling the arm support part (13) to move independently from the housing support part (11) on the horizontal plane by taking the arm support part movement pin (17) as the center.

10. The operation device of claim 9, wherein a middle block projection (1.1) of the hand-finger fixing apparatus is inclined to hold the middle three fingers of the patient.

11. The operation device of claim 10, wherein the hand-finger fixing apparatus (1) has hand fixing bands (21) in order for the fingers to be fixed on the middle block projection (1.1) and the edge projections (1.2).

12. The operation device of claim 10, wherein said hand-finger fixing apparatus (1) is larger than the edge projections (1.2) of a middle block projection (1.1) at the edge of the arm support part (13) and to form a bifurcated structure.

13. The operation device of claim 9, wherein the housing support part (11) designed in a rectangular form is connected to a rear part of the arm support part (13).

14. The operation device of claim 13 further comprising a movement pin (17) connected between the housing support part (11) designed in a rectangular form and the rear part of the arm support part (13).

15. The operation device of claim 9, wherein the flexible connection band (6) is connected to a rear part of the housing support part (11).

16. An operation device for angiographic operations applied on an arm of a patient, comprising:
    a hand-finger fixing apparatus (1) which has been designed to be larger than edge projections (1.2);
    at least one wrist air bag (8);
    a length adjustment apparatus (22) which can change a length of the operation device in accordance with the arm length of the patient;
    an elbow air bag (9);
    a housing support part (11) connected to an arm support part (13);
    at least one level adjustment apparatus (23) located on the housing support part (11);
    a flexible connection band (6);
    a power and pneumatic pumping system (2) connected to the elbow air bag (9) and wrist air bag (8) by air pipes (5); and
    a remote control unit used for operating the system;
    wherein the at least one wrist air bag (8) is located between the arm support part (13) and hand-finger fixing apparatus (1).

17. The operation device of claim 16, wherein the elbow air bag (9) is located at a rear part of the length adjustment apparatus (22) on the arm support part (13).

18. The operation device of claim 16, wherein the power and pneumatic pumping system (2) has at least one selenoid valve (3) for each air pipe (5) regulating the air flow into the system, and at least one pressure sensor (7) for each air pipe (5) which can control the air inside the system and therefore control inflation of the wrist air bag (8) and the elbow air bag (9).

* * * * *